United States Patent [19]
Michalovich

[11] Patent Number: 6,087,169
[45] Date of Patent: Jul. 11, 2000

[54] HKABY60: POLYNUCLEOTIDE ENCODING A HELIX-LOOP-HELIX UBIQUITOUS KINASE FAMILY POLYPEPTIDE

[75] Inventor: David Michalovich, London, United Kingdom

[73] Assignee: SmithKline Beecham plc, Brentford, United Kingdom

[21] Appl. No.: 09/124,476

[22] Filed: Jul. 29, 1998

[30] Foreign Application Priority Data

Aug. 4, 1997 [EP] European Pat. Off. ............... 97305868

[51] Int. Cl.[7] .......................... C12N 15/54; C12N 15/74; C12N 15/82; C12N 15/85
[52] U.S. Cl. ..................... 435/348; 435/254.1; 435/363; 435/252.3; 435/410; 536/23.2
[58] Field of Search .................... 435/194, 252.3, 435/254.2, 348, 320.1, 455, 471, 476, 69.2; 536/23.2

[56] References Cited

U.S. PATENT DOCUMENTS 5,843,721  12/1998  Rothe et al. .......................... 435/69.2
5,851,812  12/1998  Goeddel et al. ........................ 435/194

FOREIGN PATENT DOCUMENTS

WO 98/08955  3/1998  WIPO .
WO 98/37228  8/1998  WIPO .
WO 99/01541  11/1999  WIPO .

OTHER PUBLICATIONS

Régnier et al., "Identification and Characterization of an IκB Kinase" Cell. vol. 90 (2), pp. 373–383 (1997).

Woronicz et al., "IκB Kinase–β: NF–κB Activation and Complex Formation with IκB Kinase–α and NIK.", Science, vol. 278, pp. 866–869 (1997).

HGS EST# 1660004.

Primary Examiner—Charles L. Patterson, Jr.
Attorney, Agent, or Firm—William T. Han; Ratner & Prestia; William T. King

[57] ABSTRACT

HKABY60 polypeptides and polynucleotides and methods for producing such polypeptides by recombinant techniques are disclosed. Also disclosed are methods for utilizing HKABY60 polypeptides and polynucleotides in the design of protocols for the treatment of cancer, inflammatory disorders, immune disorders and viral diseases, among others, and diagnostic assays for such conditions.

9 Claims, No Drawings

HKABY60: POLYNUCLEOTIDE ENCODING A HELIX-LOOP-HELIX UBIQUITOUS KINASE FAMILY POLYPEPTIDE

This application claims the benefit of priority of European Patent Application Ser. No. 97305868.8, filed Aug. 4, 1997, and whose contents are herein incorporated in its entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the conserved helix-loop-helix ubiquitous kinase family, hereinafter referred to as HKABY60. The invention also relates to inhibiting or activating the action of such polynucleotides and polypeptides.

BACKGROUND OF THE INVENTION

A human conserved helix-loop-helix ubiquitous kinase (CHUK) has recently been shown to act in the tumor necrosis factor TNF)-interleukin-1 (IL-1) signal transduction pathway activating the nuclear factor kappa-B (NF-kappaB) transcriptional activator (C. H Regnier, et al., Cell 90:373–383, 1997). A mouse CHUK has also recently been identified (M A. Connelly and K B. Marcu, Cell.Mol.Biol.Res. 41:537–549, 1995). CHUK acts to phosphorylate the inhibitor of NF-kappa-B, I-kappaB, targeting the inhibitor for degadation and allowing NF-kappaB mediated gene activation to occur. NF-kappaB and related proteins control the expression of numerous immune and inflammatory response genes as well as viral genes and have also been implicated in malignant cell transformation (P A. Baeuerle and D. Baltimore, Cell 87:13–20, 1996; P A. Baeuerle and T. Henkel, Annu. Rev. Immunol. 12:141–179, 1995). Understanding this signal transduction pathway is therefore of significant biomedical importance.

This indicates that members of the conserved helix-loop-helix ubiquitous kinase family have potential as therapeutic targets and consequently there is a need for identification and characterization of further members of the family.

SUMMARY OF THE INVENTION

In one aspect, the invention relates to HKABY60 polypeptides and recombinant materials and methods for their production. Another aspect of the invention relates to methods for using such HKABY60 polypeptides and polynucleotides. Such uses include the treatment of cancer, inflammatory disorders, immune disorders and viral diseases, among others. In still another aspect, the invention relates to methods to identify agonists and antagonists using the materials provided by the invention, and treating conditions associated with HKABY60 imbalance with the identified compounds. Yet another aspect of the invention relates to diagnostic assays for detecting diseases associated with inappropriate HKABY60 activity or levels.

DESCRIPTION OF THE INVENTION

Definitions

The following definitions are provided to facilitate understanding of certain terms used frequently herein.

"HKABY60" refers, among others, generally to a polypeptide having the amino acid sequence set forth in SEQ ID NO:2 or an allelic variant thereof.

"HKABY60 activity or HKABY60 polypeptide activity" or "biological activity of the HKABY60 or HKABY60 polypeptide" refers to the metabolic or physiological function of said HKABY60 including similar activities or improved activities or these activities with decreased undesirable side-effects. Also included are antigenic and immunogenic activities of said HKABY60.

"HKABY60 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single-and double-stranded regions, single- and double-stranded RNA, and RNA that is mixture of single-and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann N.Y. Acad Sci (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectivley, over the length of the sequences being compared. For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), which is particularly suitable for sequences of the same or very similar length, or over shorter, defined lengths (so-called local alignment), which is more suitable for sequences of unequal length.

Methods for comparing the identity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotide or two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences which are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities are determined when the two sequences being compared are optimally aligned.

Other programs for determining % identity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and HenikoffJ G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value, as hereinbefore described.

Polypeptides of the Invention

In one aspect, the present invention relates to HKABY60 polypeptides (or HKABY60 proteins). The polypeptide of SEQ ID NO:2 is a partial peptide sequence which is the N-terminal 201 amino acid residues of the full-length HKABY60 polypeptide. The HKABY60 polypeptides of the invention include the polypeptide of SEQ ID NO:2; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Furthermore, those with at least 97–99% are highly preferred. Also included within HKABY60 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably HKABY60 polypeptides exhibit at least one biological activity of HKABY60.

The HKABY60 polypeptides may be in the form of the "mature" protein or may be a part of a larger protein such as a fusion protein or precursor. It is often advantageous to include an additional amino acid sequence which contains secretory or leader sequences, pro-sequences, sequences which aid in purification such as multiple histidine residues, or an additional sequence for stability during recombinant production.

Fragments of the HKABY60 polypeptides are also included in the invention. A fragment is a polypeptide having an amino acid sequence that is entirely the same as part, but not all, of the amino acid sequence of the aforementioned HKABY60 polypeptides. As with HKABY60 polypeptides, fragments may be "free-standing", or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HKABY60 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HKABY60 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HKABY60 activity, including those with a similar activity or an improved activity, or with a decreased undesirable activity. Also included are those that are antigenic or immunogenic in an animal, especially in a human.

Preferably, all of these polypeptide fragments retain the biological activity of the HKABY60, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted added in any combination.

The HKABY60 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HKABY60 polynucleotides. HKABY60 polynucleotides include isolated polynucleotides which encode the HKABY60 polypeptides and fragments, and polynucleotides closely related thereto. More specifically, HKABY60 polynucleotide of the invention include a polynucleotide comprising the nucleotide sequence contained in SEQ ID NO:1 encoding a partial HKABY60 polypeptide of SEQ ID NO:2, and polynucleotide having the particular sequence of SEQ ID NO:1. HKABY60 polynucleotides further include a polynucleotide comprising a nucleotide sequence that has at least 80% identity over its entire length to a nucleotide sequence encoding the HKABY60 polypeptide of SEQ ID NO:2, and a polynucleotide comprising a nucleotide sequence that is at least 80% identical to SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HKABY60 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such HKABY60 polynucleotides.

HKABY60 of the invention is structurally related to other proteins of the conserved helix-loop-helix ubiquitous kinase family, as shown by the results of sequencing the cDNA of SEQ ID NO:1 encoding the HKABY60 polypeptide of SEQ ID NO:2. The cDNA sequence of SEQ ID NO:1 contains an open reading frame (nucleotide number 173 to 775) encoding a partial polypeptide of 201 amino acids shown in SEQ ID NO:2. The amino acid sequence of SEQ ID NO:2 has about 67% identity (using Smith-Waterman) in 201 amino acid residues with Human CHUK (C. H. Regnier et al., Cell, 90:373–383, 1997). Furthermore, HKABY60 (SEQ ID NO:2) is 67% identical to mouse CHUK over 201 amino acid residues (C. H. Regnier et al., Cell, 90:373–383, 1997). The nucleotide sequence of SEQ ID NO:1 has about 67.5% identity (using Smith-Waterman) in 566 nucleotide residues with mouse CHUK (MA. Connelly and K B. Marcu, Cell. Mol. Biol. Res. 41:537–549, 1995). Thus HKABY60 polypeptides and polynucleotides of the present invention are expected to have, inter alia, similar biological functions/properties to their homologous polypeptides and polynucleotides, and their utility is obvious to anyone skilled in the art.

One polynucleotide of the present invention encoding HKABY60 may be obtained using standard cloning and screening, from a cDNA library derived from mRNA in cells of dendritic origin, prostate, skin, fetal liver and spleen using the expressed sequence tag (EST) analysis (Adams, M .D., et al. Science (1991)252:1651–1656; Adams, M D. etal., Nature, (1992)355:632–634; Adams, M D., etal., Nature (1995)377 Supp:3–174). Polynucleotides of the invention can also be obtained from natural sources such as genornic DNA libraries or can be synthesized using well known and commercially available techniques.

The nucleotide sequence encoding HKABY60 polypeptide of SEQ ID NO:2 may be identical to the polypeptide encoding sequence contained in SEQ ID NO:1 (nucleotide number 173 to 775 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of HKABY60 polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824 may also contain noncodingtag. The polynucleotide may also contain noncoding 5' and 3' sequences, such as transcribed, non-translated sequences, splicing and polyadenylation signals, ribosome binding sites and sequences that stabilize mRNA.

Further preferred embodiments are polynucleotides encoding HKABY60 variants comprise the amino acid sequence HKABY60 polypeptide of SEQ ID NO:2 in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding HKABY60 polypeptide and to isolate cDNA and genomic clones of other genes (including genes encoding homologs and orthologs from species other than ) that have a high sequence similarity to the HKABY60 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HKABY60 polypeptide, including homologs and orthologs from species other than human, comprises the steps of screening an appropriate library under stingent hybridization conditions with a labeled probe having the SEQ ID NO:1 or a fragment thereof; and isolating full-length cDNA and genomic clones containing said polynucleotide sequence. Thus in another aspect, HKABY60 polynucleotides of the present invention further include a nucleotide sequence comprising a nucleotide sequence that hybridize under stringent condition to a nucleotide sequence having SEQ ID NO:1 or a fragment thereof. Also included with HKABY60 polypeptides are polypeptide comprising amino acid sequence encoded by nucleotide sequence obtained by the above hybridization condition. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6),5× Denhardt's solution, 10 % dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY(1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HKABY60 polypeptide is to be expressed for use in screening assays, generally, it is preferred that the polypeptide be produced at the surface of the cell. In this event, the cells may be harvested prior to use in the screening assay. If HKABY60 polypeptide is secreted into the medium, the medium can be recovered in order to recover and purify the polypeptide; if produced intracellularly, the cells must first be lysed before the polypeptide is recovered.

HKABY60 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HKABY60 polynucleotides for use as diagnostic reagents. Detection of a mutated form of HKABY60 gene associated with a dysfunction will provide a diagnostic tool that can add to or define a diagnosis of a disease or susceptibility to a disease which results from under-expressions, over-expression or altered expression of HKABY60. Individuals carrying mutations in the HKABY60 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HKABY60 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985)230:1242. Sequence changes at specific locations may also be revealed by nuclease protection assays, such as RNase and S1 protection or the chemical cleavage method. See Cotton et al., Proc Natl Acad Sci USA (1985) 85:4397–4401. In another embodiment, an array of oligonucleotides probes comprising HKABY60 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996).

The diagnostic assays offer a process for diagnosing or determining a susceptibility to cancer, inflammatory disorders, immune disorders and viral diseases through detection of mutation in the HABY60 gene by the methods described.

In addition, cancer, inflammatory disorders, immune disorders and viral diseases, can be diagnosed by methods comprising determining from a sample derived from a subject an abnormally decreased or increased level of HKABY60 polypeptide or HKABY60 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HKABY60 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly cancer, inflammatory disorders, immune disorders and viral diseases, which comprises:

(a) a HKABY60 polynucleotide, preferably the nucleotide sequence of SEQ ID NO:1, or a fragment thereof;
(b) a nucleotide sequence complementary to that of (a);
(c) a HKABY60 polypeptide, preferably the polypeptide of SEQ ID NO:2, or a fragment thereof, or
(d) an antibody to a HKABY60 polypeptide, preferably to the polypeptide of SEQ ID NO:2.

It will be appreciated that in any such kit, (a), (b), (c) or (d) may comprise a substantial component.

Chromosome Assays

The nucleotide sequences of the present invention are also valuable for chromosome localisation. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Tissue Localisation

The nucleotide sequences of the present invention are also valuable for tissue localisation. Such techniques allow the determination of expression patterns of the HKABY60 polypeptides in tissues by detection of the mRNAs that encode them. These techniques include in situ hybridziation techniques and nucleotide amplification techniques, for example PCR. Such techniques are well known in the art. Results from these studies provide an indication of the normal functions of the polypeptides in the organism. In addition, comparative studies of the normal expression pattern of HKABY60 mRNAs with that of mRNAs encoded by a mutant HKABY60 gene provide valuable insights into the role of mutant HKABY60 polypeptides, or that of inappropriate expression of normal HKABY60 polypeptides, in disease. Such inappropriate expression may be of a temporal, spatial or simply quantitative nature.

Antibodies

The polypeptides of the invention or their fragments or analogs thereof, or cells expressing them can also be used as immunogens to produce antibodies immunospecific for the HKABY60 polypeptides. The term "immunospecific" means that the antibodies have substantially greater affinity for the polypeptides of the invention than their affinity for other related polypeptides in the prior art.

Antibodies generated against the HKABY60 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975)256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatogaphy.

Antibodies against HKABY60 polypeptides may also be employed to treat cancer, inflammatory disorders, immune disorders and viral diseases, among others.

Vaccines

Another aspect of the invention relates to a method for inducing an immunological response in a mammal which comprises inoculating the mammal with HKABY60 polypeptide, or a fragment thereof, adequate to produce antibody and/or T cell immune response to protect said animal from cancer, inflammatory disorders, immune disorders and viral diseases, among others. Yet another aspect of the invention relates to a method of inducing immunological response in a mammal which comprises, delivering HKABY60 polypeptide via a vector directing expression of HKABY60 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HKABY60 polypeptide wherein the composition comprises a HKABY60 polypeptide or HKABY60 gene. The vaccine formulation may further comprise a suitable carrier. Since HKABY60 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-died condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HKABY60 polypeptide of the present invention may be employed in a screening process for compounds which activate (agonists) or inhibit activation of (antagonists, or otherwise called inhibitors) the HKABY60 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, receptors, enzymes, etc., as the case may be, of the polypeptide of the present invention; or may be structural or functional mimetics of the polypeptide of the present invention. See Coligan et al., Current Protocols in Immunology 1(2) :Chapter 5 (1991).

HKABY60 polypeptides are responsible for one or more biological functions, including one or more pathologies. Accordingly, it is desirous to find compounds and drugs which stimulate HKABY60 polypeptide on the one hand and which can inhibit the function of HKABY60 polypeptide on the other hand. In general, agonists are employed for therapeutic and prophylactic purposes for such conditions as cancer, inflammatory disorders, immune disorders and viral diseases. Antagonists may be employed for a variety of therapeutic and prophylactic purposes for such conditions as cancer, inflammatory disorders, immune disorders and viral diseases.

In general, such screening procedures may involve using appropriate cells which express the HKABY60 polypeptide or respond to HKABY60 polypeptide of the present invention. Such cells include cells from mammals, yeast, Drosophila or E. coli. Cells which express the HKABY60 polypeptide (or cell membrane containing the expressed polypeptide) or respond to HKABY60 polypeptide are then contacted with a test compound to observe binding, or stimulation or inhibition of a functional response. The ability of the cells which were contacted with the candidate compounds is compared with the same cells which were not contacted for HKABY60 activity.

The assays may simply test binding of a candidate compound wherein adherence to the cells bearing the HKABY60 polypeptide is detected by means of a label directly or indirectly associated with the candidate compound or in an assay involving competition with a labeled competitor. Further, these assays may test whether the candidate compound results in a signal generated by activation of the HKABY60 polypeptide, using detection systems appropriate to the cells bearing the HKABY60 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a HABY60 polypeptide to form a mixture, measuring HABY60 activity in the mixture, and comparing the HKABY60 activity of the mixture to a standard.

The HKABY60 cDNA, protein and antibodies to the protein may also be used to configure assays for detecting the effect of added compounds on the production of HKABY60 mRNA and protein in cells. For example, an ELISA may be constructed for measuring secreted or cell associated levels of HKABY60 protein using monoclonal and polyclonal antibodies by standard methods known in the art, and this can be used to discover agents which may inhibit or enhance the production of HKABY60 (also called antagonist or agonist, respectively) from suitably manipulated cells or tissues.

The HKABY60 protein may be used to identify membrane bound or soluble receptors, if any, through standard receptor binding techniques known in the art. These include, but are not limited to, ligand binding and crosslinking assays in which the HKABY60 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of HKABY60 which compete with the binding of HKABY60 to its receptors, if any. Standard methods for conducting screening assays are well understood in the art.

Examples of potential HKABY60 polypeptide antagonists include antibodies or, in some cases, oligonucleotides or proteins which are closely related to the ligands, substrates, receptors, enzymes, etc., as the case may be, of the HKABY60 polypeptide, e.g., a fragment of the ligands, substrates, receptors, enzymes, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for HKABY60 polypeptides; or compounds which decrease or enhance the production of HKABY60 polypeptides, which comprises:

(a) a HKABY60 polypeptide, preferably that of SEQ ID NO:2;

(b) a recombinant cell expressing a HKABY60 polypeptide, preferably that of SEQ ID NO:2;

(c) a cell membrane expressing a HKABY60 polypeptide; preferably that of SEQ ID NO:2; or (d) antibody to a HKABY60 polypeptide, preferably that of SEQ ID NO: 2.

It will be appreciated that in any such kit, (a), (b), (c) or (d) may comprise a substantial component.

Prophylatic and Therapeutic Methods

This invention provides methods of treating abnormal conditions such as, cancer, inflammatory disorders, immune disorders and viral diseases, related to both an excess of and insufficient amounts of HKABY60 polypeptide activity.

If the activity of HKABY60 polypeptide is in excess, several approaches are available. One approach comprises administering to a subject an inhibitor compound (antagonist) as hereinabove described along with a pharmaceutically acceptable carrier in an amount effective to inhibit the function of the HKABY60 polypeptide, such as, for example, by blocking the binding of ligands, substrates, receptors, enzymes, etc., or by inhibiting a second signal, and thereby alleviating the abnormal condition. In another approach, soluble forms of HKABY60 polypeptides still capable of binding the ligand, substrate, enzymes, receptors, etc. in competition with endogenous HKABY60 polypeptide may be administered. Typical embodiments of such competitors comprise fragments of the HKABY60 polypeptide.

In still another approach, expression of the gene encoding endogenous HKABY60 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee et al., Nucleic Acids Res (1979) 6:3073; Cooney et al., Science (1988) 241:456; Dervan et al., Science (1991) 251:1360. These oligomers can be administered per se or the relevant oligomers can be expressed in vivo.

For treating abnormal conditions related to an under-expression of HKABY60 and its activity, several approaches are also available. One approach comprises administering to a subject a therapeutically effective amount of a compound which activates HKABY60 polypeptide, i.e., an agonist as described above, in combination with a pharmaceutically acceptable carrier, to thereby alleviate the abnormal condition. Alternatively, gene therapy may be employed to effect the endogenous production of HKABY60 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vio and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of HKABY60 polypeptides in combination with a suitable pharmaceutical carrier.

Formulation and Administration

Peptides, such as the soluble form of HKABY60 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alterative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

All publications, including but not limited to patents and patent applications, cited in this specification are herein incorporated by reference as if each individual publication were specifically and individually indicated to be incorporated by reference herein as though fully set forth.

Sequence Information
Seq ID NO:1
  1 GNAAGTGTTTGAGGAAGTCGCGCCGCGCTGCCCGCGTTAAGATTCCCGCATTTTAATGTT

61 TTCAGGGGGTGTCATAGCCCCGGGTTTGGCCGCCCCAGCCCCGCCTTCCCCGCCCCGGG

121 GAGCCCGCCCCCTGCCCCGCGTCCCTGCCGACAGAGTTAGCACGACATCAGTATGAGCTG

181 GTCACCTTCCCTGACAACGCAGACATGTGGGGCCTGGGAAATGAAAGAGCGCCTTGGGAC
    AGGGGGATTTGGAAATGTCATCCGATGGCACAATCAGGAAACAGGTGAGCAGATTGCCAT

301 CAAGCAGTGCCGGCAGGAGCTCAGCCCCCGGAACCGAGAGCGGTGGTGCCTGGAGATCCA

361 GATCATGAGAAGGCTGACCCACCCCAATGTGGTGGCTGCCCGAGATGTCCCTGAGGGGAT

421 GCAGAACTTGGCGCCCAATGACCTGCCCCTGCTGGCCATGGAGTACTGCCAAGGAGGAGA

481 TCTCCGGAAGTACCTGAACCAGTTTGAGAACTGCTGTGGTCTGCGGGAAGGTGCCATCCT

541 CACCTTGCTGAGTGACATTGCCTCTGCGCTTAGATACCTTCATGAAAACAGAATCATCCA

601 TCGGGATCTAAAGCCAGAAAACATCGTCCTGCAGCAAGGAGAACAGAGGTTAATACACAA

661 AATTATTGACCTAGGATATGCCAAGGAGCTGGATCAGGGCAGTCTTTGCACATCATTCGT

721 GGGGANCCTGCAGTACCTGGCCCCAGAGCTACTGGAGCAGCAGAAGTACACAGTG

SEQ ID NO:2
  1 MSWSPSLTTQTCGAWEMKERLGTGGFGNVIRWHNQETGEQIAIKQCRQELSPRNRERWCL

61 EIQIMRRLTHPNVVAARDVPEGMQNLAPNDLPLLAMEYCQGGDLRKYLNQFENCCGLREG

121 AILTLLSDIASALRYLHENRIIHRDLKPENIVLQQGEQRLIHKIIDLGYAKELDQGSLCT

181 SFVGXLQYLAPELLEQQKYTV

---

What is claimed is:

1. An isolated polynucleotide comprising a nucleotide sequence which has at least 95% identity to that of SEQ ID NO:1, said identity being over the entire length of SEQ ID NO:1 and calculated using FASTA wherein sequences are aligned to give maximum correlation between the sequences.

2. An isolated polynucleotide comprising the polynucleotide sequence set forth in SEQ ID NO:1.

3. The isolated polynucleotide of claim 2 which consists of the polynucleotide sequence set forth in SEQ ID NO: 1.

4. An isolated polynucleotide obtainable by screening an appropriate library under stringent hybridization conditions with a labeled probe having the sequence of SEQ ID NO:1 or a fragment thereof, said hybridization conditions comprising: overnight incubation of filters comprising said isolated polynucleotide at 42° C. in a solution comprising: 50% formamide, 5×SSC, 50 mM sodium phosphate having pH7.6, 5×Denhardt's solution, 10 % dextran sulfate, and 20 microgram/ml denatured, sheared salmon sperm DNA, followed by washing the filters in 0. 1×SSC at about 65° C.

5. An isolated polynucleotide comprising a nucleotide sequence which is fully complementary to said isolated polynucleotide in any one of claims 1–4.

6. An expression system comprising a polynucleotide as set forth in SEQ ID NO:1 when said expression system is present in a compatible host cell.

7. A process for producing a recombinant host cell comprising transforming or transfecting a cell with the expression system of claim 6.

8. A recombinant host cell produced by the process of claim 7.

9. A membrane of a recombinant host cell of claim 8.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 775 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
GNAAGTGTTT GAGGAAGTCG CGCCGCGCTG CCCGCGTTAA GATTCCCGCA TTTTAATGTT      60

TTCAGGGGGG TGTCATAGCC CCGGGTTTGG CCGCCCCAGC CCCGCCTTCC CGCCCCGGG      120

GAGCCCGCCC CCTGCCCCGC GTCCCTGCCG ACAGAGTTAG CACGACATCA GTATGAGCTG     180

GTCACCTTCC CTGACAACGC AGACATGTGG GGCCTGGGAA ATGAAAGAGC GCCTTGGGAC     240

AGGGGGATTT GGAAATGTCA TCCGATGGCA CAATCAGGAA ACAGGTGAGC AGATTGCCAT     300

CAAGCAGTGC CGGCAGGAGC TCAGCCCCCG GAACCGAGAG CGGTGGTGCC TGGAGATCCA     360

GATCATGAGA AGGCTGACCC ACCCCAATGT GGTGGCTGCC CGAGATGTCC CTGAGGGGAT     420

GCAGAACTTG GCGCCCAATG ACCTGCCCCT GCTGGCCATG GAGTACTGCC AAGGAGGAGA     480

TCTCCGGAAG TACCTGAACC AGTTTGAGAA CTGCTGTGGT CTGCGGGAAG GTGCCATCCT     540

CACCTTGCTG AGTGACATTG CCTCTGCGCT TAGATACCTT CATGAAAACA GAATCATCCA     600
```

```
TCGGGATCTA AAGCCAGAAA ACATCGTCCT GCAGCAAGGA GAACAGAGGT TAATACACAA      660

AATTATTGAC CTAGGATATG CCAAGGAGCT GGATCAGGGC AGTCTTTGCA CATCATTCGT      720

GGGGANCCTG CAGTACCTGG CCCCAGAGCT ACTGGAGCAG CAGAAGTACA CAGTG          775

(2) INFORMATION FOR SEQ ID NO:2:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Ser Trp Ser Pro Ser Leu Thr Thr Gln Thr Cys Gly Ala Trp Glu
 1               5                  10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Xaa Leu Gln Tyr Leu Ala Pro Glu
            180                 185                 190

Leu Leu Glu Gln Gln Lys Tyr Thr Val
            195                 200
```